United States Patent [19]

Gassman

[11] 4,252,723
[45] Feb. 24, 1981

[54] AIR OXIDATION OF OXINDOLES TO ISATINS

[75] Inventor: Paul G. Gassman, St. Paul, Minn.

[73] Assignee: Regents of the University of Minnesota, Minneapolis, Minn.

[21] Appl. No.: 2,951

[22] Filed: Jan. 12, 1979

[51] Int. Cl.³ .......................................... C07D 209/38
[52] U.S. Cl. .................................................. 260/325 R
[58] Field of Search .................................. 260/325 R

[56] References Cited

U.S. PATENT DOCUMENTS

| | | | |
|---|---|---|---|
| 646,841 | 4/1900 | Knietsch | 260/325 R |
| 3,897,451 | 7/1975 | Gassman | 260/325 R |
| 3,983,242 | 9/1976 | Hardtmann et al. | 260/325 R |
| 4,186,132 | 1/1980 | Gassman | 260/325 R |
| 4,188,325 | 2/1980 | Gassman et al. | 260/325 R |

OTHER PUBLICATIONS

Gassman et al., J. Org. Chem., vol. 42, pp. 1344–1348 (1977).

*Primary Examiner*—Alton D. Rollins
*Attorney, Agent, or Firm*—Gordon W. Hueschen

[57] ABSTRACT

An aniline is converted to a 3-lower hydrocarbonthiooxindole by processes already known in the art and then air oxidized in an inert liquid vehicle in the presence of a base. The inert liquid vehicle advantageously is aprotic and the base is non-nucleophilic. Also, the aprotic liquid vehicle is desirably solvent for the starting 3-lower hydrocarbonthiooxindole and the non-nucleophilic base.

17 Claims, No Drawings

AIR OXIDATION OF OXINDOLES TO ISATINS

The invention described herein was made in the course of work done under a grant or award from the National Science Foundation.

BACKGROUND OF THE INVENTION

The invention is directed to a process for preparing isatins and to novel compounds produced therein, and is particularly directed to a process in which isatins can be prepared from anilines with a wide variety of substituents.

Isatins have long been considered as valuable synthetic intermediates in the preparation of both pharmaceuticals and dyes. See, for example, the chapter on Indigoid Dyes, pp. 551–576, *The Chemistry of Synthetic Dyes*, Reinhold Publishing Co., New York, N.Y. (1955). As a consequence, considerable effort has been devoted to developing useful synthetic approaches to the preparation of this class of compounds from readily available starting materials, particularly the anilines. Unfortunately, the processes heretofore available were limited in regard to the type of substituents which could be present in the starting anilines due to the fact that such processes required catalysis by strong acids. Thus, Sandmeyer, *Helv. Chim. Acta*, 2, 234 (1919) discloses a process in which aniline is reacted with trichloroacetaldehyde and then with hydroxylamine in base. The resulting isonitrosoacetanilide is then heated in sulfuric acid. Also, Stolle, *J. Prakt. Chem.*, 105, 137 (1922) discloses a process in which an aniline is treated with oxalyl chloride followed by Friedel-Crafts type acylation in the presence of a strong Lewis acid. Since both methods require electrophilic attack on the aromatic ring, the presence of strong electron-withdrawing groups in the aniline, especially in the meta position, tend to inhibit the reaction. For example, a nitro group in the meta position effectively blocks these syntheses.

A new method for the general synthesis of isatins was recently described by P. G. Gassman, et al., *J. Org. Chem.*, 42, 1344 (1977). The process involves the chlorination of 3-lower hydrocarbonthiooxindoles, readily available from anilines, followed by hydrolysis, and has the advantage that the starting 3-lower hydrocarbonthiooxindoles can readily be prepared from anilines having a broad spectrum of electron-withdrawing and electron-donating substituents. It has the disadvantage, however, that mercuric oxide and boron trifluoride-etherate are used in the hydrolysis and consequently involves the usual problems attending the large scale use of these reagents.

OBJECTS OF THE INVENTION

It is an object of the invention to provide a new and improved process for making isatins from anilines. It is a further object to provide a simplified process for converting 3-lower hydrocarbonthiooxindoles into the corresponding isatins. It is a further object of the invention to avoid the disadvantages of the prior art and to obtain advantages as will appear as the description proceeds.

BRIEF DESCRIPTION OF THE INVENTION

The invention is directed to a process for making isatins by subjecting a 3-lower hydrocarbonthiooxindole to gaseous oxygen in the presence of a base, advantageously a non-nucleophilic base, wherein the 3-lower hydrocarbonthiooxindole is converted directly to the desired isatin. By non-nucleophilic base is meant a base that does not give up or donate electrons. Potassium tert-butoxide is a suitable such non-nucleophilic base. Advantageously, the oxidation is effected with ambient air in a substantially inert liquid vehicle which advantageously is aprotic and anhydrous.

The starting 3-lower hydrocarbonthiooxindoles used in the process of the invention can be prepared from anilines by first converting the aniline to an N-haloaniline by oxidative halogenation with a source of positive halogen as described in U.S. Pat. No. 3,972,894, reacting the formed N-haloaniline with a β-lower hydrocarbonthiocarboxylic ester or β-lower hydrocarbonthiocarboxylic amide to form the azasulfonium salt, and rearranging the latter to form a 2-(lower hydrocarbonthio-carboxymethyl) aniline in which the carboxy group is in the form of an ester or amide. The resulting substituted aniline is then cyclized by heating to form the desired 3-lower hydrocarbonthiooxindole starting compound.

It has been found in accordance with the invention that the oxidation with gaseous oxygen in the presence of a non-nucleophilic base is most effective to convert 3-lower hydrocarbonthiooxindoles, having a large spectrum of electron-withdrawing and electron-donating substituents, directly to the corresponding isatins.

Processes applicable for the conversion of anilines with such a wide spectrum of electron-withdrawing and electron-donating substituents to the desired 3-lower hydrocarbonthiooxindoles are described in U.S. Pat. Nos. 3,972,894, 3,897,451, 3,996,264, 3,954,797, 3,960,926, and 3,985,756, and in Gassman et al., *J. Am. Chem. Soc.*, 96, 5508 (1974), and Gassman et al., *J. Am. Chem. Soc.*, 96, 5512 (1974), inter alia. These processes accordingly are suitable for preparation of the starting compounds of the invention.

The oxidation of the starting 3-lower hydrocarbonthiooxindole can be effected advantageously by passing atmospheric air into a substantially inert liquid vehicle having dispersed therein the starting 3-lower hydrocarbonthiooxindole and a non-nucleophilic base. The dispersion can be physical or molecular (solution). Thus, one or the other or both of the starting 3-lower hydrocarbonthiooxindole and the base can be dissolved in a substantially inert solvent or physically dispersed in an inert liquid vehicle.

By a substantially inert liquid vehicle or solvent is meant one which does not prevent the formation of desired product. Thus, while advantageously an aprotic liquid vehicle, such as diethyl ether or tetrahydrofuran, is used because oxidation with gaseous oxygen in the presence of water or other protic solvent results in the conversion of some of the isatins produced to anthranilic acids, it is to be understood that, in the broader aspects of the invention, water is a substantially inert liquid vehicle. Thus, while with water, as much as two parts anthranilic acid may be obtained for each part of isatin, nonetheless, the desired product is also obtained. However, when an aprotic liquid vehicle and a non-nucleophilic base are used, essentially no anthranilic acid is produced. Thus, in the preferred form of the invention, the starting 3-lower hydrocarbonthiooxindole and the non-nucleophilic base are dissolved in diethyl ether or anhydrous tetrahydrofuran, or like inert aprotic solvent, and aerated with gaseous oxygen without heating. Room temperature or thereabout is satisfactory. Lower temperatures are preferred, at least for a portion of the reaction period, e.g., about zero degrees Centigrade. The reaction will ordinarily be complete in less than thirty hours. Advantageously, the aeration is effected with ambient air cooled to about zero degrees Centigrade, e.g., about −20° to about +10° Centigrade, for two to ten hours, and then at about room temperature until the conversion is complete. Room temperature is usually the maximum temperature required. Cooling may be employed to maintain the temperature at about room temperature if desired. Elevated temperatures may be employed but are not required. Ordinarily, the reaction is complete in less than thirty hours, e.g., in ten to thirty hours. The product is isolated either by extraction or filtration and recrystallized and is sufficiently free of by-products that chromatography is not required.

It is to be understood that the invention, in its broader aspects, is not limited to atmospheric or ambient air, but that any source of gaseous oxygen can be used; and that in place of potassium t-butoxide as the non-nucleophilic base, there can be substituted other bases, for example, other alkali metal alkoxides, e.g., sodium isopropoxide, and alkali metal amides, especially alkali metal alkyl amides such as lithium diisopropyl amide, and the like. Nucleophilic bases may also be employed, such as alkali metal carbonates, bicarbonates, and hydroxides, illustratively sodium or potassium hydroxide, carbonate, or bicarbonate, but such nucleophilic reagents result in ring cleavage and are accordingly not preferred.

In place of the diethyl ether or anhydrous tetrahydrofuran, there can be substituted other solvents, preferably aprotic solvents, for example dioxane or a related aprotic solvent. Protic solvents such as methanol, ethanol, isopropanol, or other alcohols may also be employed, but are less desirable due to side reactions inherent with their employment. Protic acidic solvents which cannot contain the necessary base can obviously not be employed, it being necessary only that the solvent or other liquid vehicle employed be inert or non-reactive with the reactants and the reaction products under the conditions employed.

Unless otherwise qualified, "aerated" means aerated with atmospheric or ambient air.

The molar ratio of oxygen to starting lower-hydrocarbon, e.g., methyl, thiooxindole is theoretically stoichiometric. However, since some of the gaseous oxygen is lost in the process, an excess is ordinarily employed, especially when atmospheric or ambient air is the oxidizing medium involved. On the other hand, the molar ratio of the base employed to the starting lower-hydrocarbon, e.g., methyl, thiooxindole is preferably about the theoretical equimolar amount. More or less can be used. Less than such an amount results in a slower rate of reaction and incomplete reaction, whereas more than such an amount results in reduced yields due to decomposition of the desired reaction product.

The invention may be more fully understood by reference to the accompanying reaction scheme based in part on the processes of U.S. Pat. Nos. 3,972,894, 3,897,451, and 3,996,264.

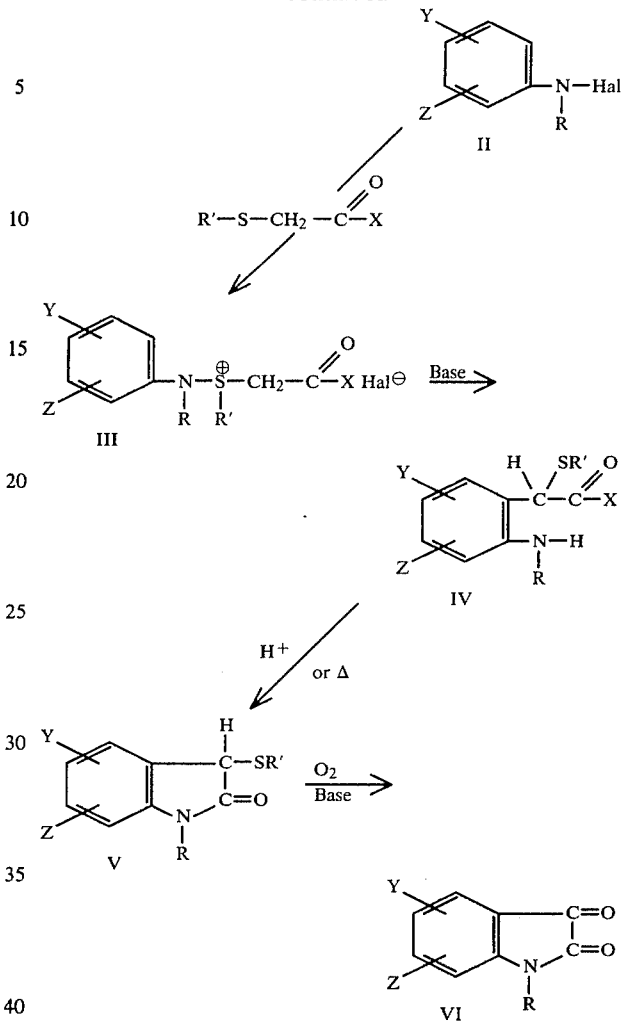

In the above formulas, X is —OR$^3$ or —N(R$^4$)$_2$, wherein R$^3$ and R$^4$ are lower hydrocarbon radicals, and Y, Z, R, and R' have the same values, e.g., as in U.S. Pat. No. 3,972,894. Thus, Y and Z can conveniently and independently be hydrogen or a substituent which does not donate electrons more strongly than a methoxy group in the meta position. Examples of such substituents include halogen, i.e., fluorine, chlorine, bromine, and iodine, nitro, cyano, lower-alkyl, lower-alkoxy, lower-acyloxy, carbonyloxylower-alkyl (carbalkoxy) and carbonyloxy-phenyl. Y and Z can also be trifluoromethyl. The substituent R in the foregoing reaction sequence can be hydrogen or a lower-hydrocarbon radical, as below defined, free of aliphatic unsaturation. By the term "lower", as used herein, is meant up to and including nine carbon atoms. R' can be a lower-hydrocarbon radical, for example, lower alkyl, e.g., methyl, ethyl, propyl, isopropyl, butyl, amyl, hexyl, heptyl, octyl, or nonyl, phenyl, or phenyllower-alkyl, e.g., benzyl, phenethyl, phenpropyl, or the like. When electron-donating substituents are desired for Z and/or Y, such as lower-alkoxy, e.g., methoxy, or diloweralkylamino, such as dimethylamino or diethylamino, in the starting lower-hydrocarbonthiooxindole, the procedure of U.S. Pat. No. 3,954,797, 3,960,926, or 3,985,756 may conveniently be employed. Such procedure representatively involves reaction of a chlorine: methylthio-2-propanone complex and a substituted or unsubstituted aniline, such as p-anisidine, via an intermediate azasulfonium halide salt. Since any phenyl ring substituents are in place in the aniline starting material, the range of substitutents is indeed very broad, as will be recognized by one skilled in the art.

DETAILED DESCRIPTION OF THE INVENTION

The following examples are given by way of illustration only. Parts and percentages herein are by weight unless otherwise specified. The table lists yields and melting points obtained in representative of the following examples. In general, contamination by anthranilic acid was not a problem, and in all the examples purification of the product was achieved by recrystallization without any prior chromatography.

TABLE

| Oxindole | % Yield of Isatin | Mp, °C. | Lit. mp, °C. |
| --- | --- | --- | --- |
| 3-Methylthiooxindole | 32 | 199–200 | 200–202, 200–201 |
| 5-Carboethoxy-3-methylthiooxindole | 60 | 205–206 | 206–207 |
| 5-Methyl-3-methylthiooxindole | 41 | 184–185 | 185–187 |
| 7-Methyl-3-methylthiooxindole | 40 | 268–270 | 270–272, 267 |
| 5-Chloro-3-methylthiooxindole | 49 | 246–247 | 249–252, 247 |
| 5-Methoxy-3-methylthiooxindole | 27 | 201–203 | 202–204, 201–202 |
| 5-Cyano-3-methylthiooxindole | 35 | 273–274(dec.) | 270–272(dec.) |

GENERAL PROCEDURE

In a general procedure, 0.3 to 2.0 g of sublimed potassium t-butoxide was suspended in 200–250 ml of dry ether or tetrahydrofuran at 0° C. and an equimolar amount of the corresponding 3-methylthiooxindole was added. The solution immediately became colored. The reaction mixture was then stirred and aerated at 0° C. for 4–9 h, and then at 25° C. for 15–20 h. A solution of 0.2–1.4 ml of concentrated hydrochloric acid in 20–50 ml of water was added to the reaction mixture and stirring was continued for 20–30 minutes. The product was then isolated, by either extraction or filtration, and recrystallized.

EXAMPLE 1: Isatin

According to the general procedure, 0.48 g of 3-methylthiooxindole and an equimolar quantity (E.Q.) of sublimed potassium t-butoxide in 200 ml of dry diethyl ether was aerated for 4 h at 0° C. and 20 h at 25° C. Acidification with 0.22 ml of conc. hydrochloric acid in 25 ml of water followed by extraction with ether, drying of the extracts over anhydrous magnesium sulfate, filtration, and evaporation of the filtrate gave an orange solid. Recrystallization from chloroform gave 0.13 g (32% yield) of pure isatin, mp 199°–200° C.

EXAMPLE 2: 5-Carboethoxyisatin

According to the general procedure, 4.06 g of 5-carboethoxy-3-methylthiooxindole and an E.Q. of sublimed potassium t-butoxide in 250 ml of dry tetrahydrofuran was stirred and aerated for 6 h at 0° C. and 18 h at 25° C. Acidification with 1.35 ml of conc. hydrochloric acid in 25 ml of water, followed by extraction with ether and normal workup (vide supra), gave a yellow solid which was recrystallized from ethyl acetate to yield 2.20 g (60%) of 5-carboethoxyisatin, mp 205°–206° C.

EXAMPLE 3: 5-Methylisatin

According to the general procedure, 1.58 g of 5-methyl-3-methylthiooxindole and an E.Q. of sublimed potassium t-butoxide in 250 ml of dry tetrahydrofuran was stirred and aerated for 5 h at 0° C. and 19 h at 25° C. Acidification with 0.68 ml of conc. hydrochloric acid in 50 ml of water, followed by extraction with ethyl acetate and normal workup (vide supra), gave 1.21 g of an orange solid. Recrystallization from 95% ethanol gave 0.54 g (41% yield) of 5-methylisatin, mp 184°–185° C.

EXAMPLE 4: 7-Methylisatin

Utilizing the general procedure, 3.30 g of 7-methyl-3-methylthiooxindole and an E.Q. of sublimed potassium t-butoxide in 250 ml of tetrahydrofuran was stirred and vigorously aerated for 6 h at 0° C. and 18 h at 25° C. Acidification with 1.42 ml of conc. hydrochloric acid in 20 ml of water, followed by addition of a saturated brine solution, gave an organic layer which was separated and worked up as described above to give 1.98 g of crude product. Recrystallization from methanol gave 1.09 g (40% yield) of 7-methylisatin, mp 268°–270° C.

EXAMPLE 5: 5-Chloroisatin

According to the general procedure, 2.10 g of 5-chloro-3-methylthiooxindole and an E.Q. of sublimed potassium t-butoxide in 250 ml of tetrahydrofuran was stirred and aerated for 4 h at 0° C. and 20 h at 25° C. Acidification with 0.8 ml of conc. hydrochloric acid in 25 ml of water resulted in the precipitation of an orange solid (1.10 g), which was collected by filtration. Addition of a saturated sodium chloride solution to the filtrate gave an organic phase which was separated and worked up as described above to give an additional 0.57 g of orange solid. Recrystallization of the crude product from 95% ethanol gave 0.90 g (49% yield), of 5-chloroisatin, mp 246°–247° C.

EXAMPLE 6: 5-Methoxyisatin

Oxidation, according to the general procedure, of 1.80 g of 5-methoxy-3-methylthiooxindole and an E.Q. of sublimed potassium t-butoxide in 250 ml of dry tetrahydrofuran was carried out for 6 h at 0° C. and 18 h at 25° C. Acidification with 0.72 ml of conc. hydrochloric acid in 25 ml of water, followed by extraction with ether and a standard workup procedure (vide supra), gave a dark red solid which was recrystallized from methanol to give 0.42 g (27% yield) of 5-methoxyisatin, mp 201°–203° C.

EXAMPLE 7: 5-Cyanoisatin

According to the general procedure, using an equimolar amount of potassium t-butoxide, 0.62 g of 5-cyano-3-methylthiooxindole in 200 ml of dry tetrahydrofuran was stirred and aerated for 9 h at 0° C. and 15 h at 25° C. Acidification with 0.25 ml of conc. hydrochloric acid in 25 ml of water, followed by extraction with ether and standard workup (vide supra), gave an orange solid. Recrystallization from 95% ethanol gave 0.18 g (35% yield) of 5-cyanoisatin, mp 273°–274° C. (dec.).

EXAMPLE 8:

By substituting, in Example 1, the potassium t-butoxide by sodium carbonate, sodium bicarbonate, or potassium hydroxide, and the diethyl ether by aqueous methanol, there is obtained a mixture of two parts anthranilic acid and one part isatin.

EXAMPLES 9–18:

In the same manner as given under general procedure and Example 1, the following reactions are carried out using the specified starting materials and with production of the specified product.

| Starting Material | Product |
| --- | --- |
| 9. 4-trifluoromethyl-3-methylthiooxindole | 4-trifluoromethyl-isatin |
| 10. 5-trifluoromethyl-3-methylthiooxindole | 5-trifluoromethyl-isatin |
| 11. 1-methyl-3-methylthiooxindole | 1-methylisatin |
| 12. 7-methoxy-3-methylthiooxindole | 7-methoxyisatin |
| 13. 4-acetyl-3-methylthiooxindole | 4-acetylisatin |
| 14. 4-carbomethoxy-3-methylthiooxindole | 4-carbomethoxy-isatin |
| 15. 3-ethylthiooxindole | isatin |
| 16. 3-phenylthiooxindole | isatin |
| 17. 3-benzylthiooxindole | isatin |
| 18. 5-dimethylamino-3-methylthiooxindole | 5-dimethylamino-isatin |

It is to be understood that the invention is not to be limited to the exact details of operation or structure shown and described, as obvious modifications and equivalents will be apparent to one skilled in the art.

I claim:

1. A process for making isatins which comprises subjecting a 1-hydrogen or lower-hydrocarbon free of aliphatic unsaturation-3-$C_1$–$C_9$ alkyl, aryl, or aralkyl-thiooxindole, wherein the phenyl ring of the oxindole nucleus is unsubstituted or substituted with a substituent selected from the group consisting of hydrogen, halogen, nitro, cyano, trifluoromethyl, lower-alkyl, lower-alkoxy, alkanoyl, lower-acyloxy, carbonloxy-lower alkyl, carbonyloxyphenyl, and diloweralkyl amino, to gaseous oxygen in a substantially inert liquid vehicle in the presence of a base.

2. The process of claim 1, in which the inert liquid vehicle is aprotic and the base is non-nucleophilic.

3. The process of claim 2, in which the non-nucleophilic base is potassium t-butoxide.

4. The process of claim 3, in which the inert vehicle is dry diethyl ether or anhydrous tetrahydrofuran.

5. The process of claim 1, in which the 3-hydrocarbonthiooxindole has the formula

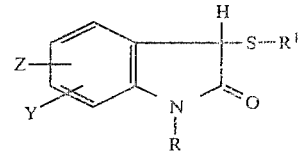

wherein Z and Y are hydrogen, halogen, nitro, cyano, trifluoromethyl, lower-alkyl, lower-alkoxy, lower-alkanoyl, lower-acyloxy carbonyloxy-lower alkyl, or carbonyloxy-phenyl;

R is hydrogen or a $C_1$–$C_9$ alkyl, aryl, or aralkyl group; and $R^1$ is lower-alkyl, phenyl, or phenyllower-alkyl.

6. The process of claim 5, in which the inert liquid vehicle is aprotic and the base is non-nucleophilic.

7. The process of claim 6, in which the non-nucleophilic base is potassium t-butoxide.

8. The process of claim 7, in which the inert vehicle is dry diethyl ether or anhydrous tetrahydrofuran.

9. The process of claim 6, in which the reaction temperature is not greater than about room temperature.

10. The process of claim 9, in which the reaction mixture is initially maintained at a temperature of about 0° C. and in the final stages is raised to about room temperature.

11. The process of claim 5, wherein $R^1$ is lower-alkyl.

12. The process of claim 5, wherein $R^1$ is methyl.

13. The process of claim 2, in which the gaseous oxygen is provided by atmospheric or ambient air.

14. The process of claim 2, in which the non-nucleophilic base is an alkali metal alkoxide.

15. The process of claim 6, in which the gaseous oxygen is provided by atmospheric or ambient air.

16. The process of claim 6, in which the non-nucleophilic base is an alkali metal alkoxide.

17. Process of claim 5, wherein Z and Y are selected from hydrogen, methyl, methoxy, cyano, chloro, carbomethoxy, carboethoxy, trifluoromethyl, acetyl, and dimethylamino; $R^1$ is a methyl, ethyl, phenyl, or benzyl group, and R is hydrogen or methyl.

* * * * *

UNITED STATES PATENT AND TRADEMARK OFFICE
CERTIFICATE OF CORRECTION

PATENT NO. : 4,252,723
DATED : February 24, 1981
INVENTOR(S) : Paul G. Gassman

It is certified that error appears in the above-identified patent and that said Letters Patent are hereby corrected as shown below:

Col. 3, line 59; insert comma (,) between "scheme" and "based"

Col. 7, line 48; "carbonloxy-lower" should read -- carbonyloxy-lower --

Col. 8, last word in line 18; delete "lower-"

Col. 8, line 19; insert comma (,) between "lower-acyloxy" and "carbonyloxy-lower"

Signed and Sealed this

Fourteenth Day of July 1981

[SEAL]

*Attest:*

*Attesting Officer*

GERALD J. MOSSINGHOFF

*Commissioner of Patents and Trademarks*